United States Patent
Geebelen et al.

(10) Patent No.: US 10,231,847 B2
(45) Date of Patent: Mar. 19, 2019

(54) IMPLANT FIXATION SYSTEM AND METHODS

(71) Applicant: MATERIALISE N.V., Leuven (BE)

(72) Inventors: Benjamin Geebelen, Haasrode (BE); Nils Faber, Leuven (BE)

(73) Assignee: Materialise N.V., Leuven (BE)

( * ) Notice: Subject to any disclaimer, the term of this patent is extended or adjusted under 35 U.S.C. 154(b) by 548 days.

(21) Appl. No.: 14/822,663

(22) Filed: Aug. 10, 2015

(65) Prior Publication Data
US 2015/0342754 A1 Dec. 3, 2015

Related U.S. Application Data (63) Continuation of application No. PCT/EP2014/052568, filed on Feb. 10, 2014.
(Continued)

(51) Int. Cl.
*A61F 2/46* (2006.01)
*A61F 2/30* (2006.01)
(Continued)

(52) U.S. Cl.
CPC ........ *A61F 2/4603* (2013.01); *A61F 2/30749* (2013.01); *B22F 3/1055* (2013.01);
(Continued)

(58) Field of Classification Search
CPC ................ A61F 2/30749; A61F 2/4603; A61F 2/30942; A61F 2002/30579; A61F 2002/4623; A61F 2240/001
See application file for complete search history.

(56) References Cited

U.S. PATENT DOCUMENTS 3,024,785 A 3/1962 Dobelle
4,237,875 A * 12/1980 Termanini .......... A61B 17/7225
606/63

(Continued)

FOREIGN PATENT DOCUMENTS

GB 2447018 A 9/2008

OTHER PUBLICATIONS

International Search Report and Written Opinion dated Jun. 10, 2014 issued on related PCT Application No. PCT/EP2014/052568, filed Feb. 10, 2014 and published as WO/2014/122313 dated Aug. 14, 2014.

*Primary Examiner* — Kevin T Truong
*Assistant Examiner* — Tracy Kamikawa
(74) *Attorney, Agent, or Firm* — Patterson & Sheridan, LLP (57) ABSTRACT

The implant fixation systems disclosed herein include an implant manufactured with, or coupled to, one or more implant fixation devices used to secure the implant to bone. Various implant fixation device embodiments have an engagement element with a concave engagement tip, a guiding element defining a planned trajectory along which the engagement element is configured to move, and an adjustment element configured to move the engagement element along the planned trajectory. Moving the engagement element along the planned trajectory causes the concave engagement tip to enter a bone in a first position and rotate within the bone to a second position. Continuing to move the engagement element along the planned trajectory may cause the concave engagement tip to undergo translational movement from the second position to a third position, thereby pulling the implant towards the bone and exerting compression forces on the bone.

8 Claims, 7 Drawing Sheets

Related U.S. Application Data (60) Provisional application No. 61/763,392, filed on Feb. 11, 2013.

(51) Int. Cl.
  *B22F 3/105* (2006.01)
  *B22F 5/00* (2006.01)
  *B33Y 10/00* (2015.01)
  *B33Y 50/00* (2015.01)
  *B33Y 80/00* (2015.01)

(52) U.S. Cl.
  CPC ...... *B22F 5/00* (2013.01); *A61F 2002/30579* (2013.01); *A61F 2002/4623* (2013.01); *A61F 2240/001* (2013.01); *B22F 2003/1057* (2013.01); *B33Y 10/00* (2014.12); *B33Y 50/00* (2014.12); *B33Y 80/00* (2014.12); *Y10T 29/49828* (2015.01)

(56) References Cited

U.S. PATENT DOCUMENTS

| | | | |
|---|---|---|---|
| 5,057,103 A | 10/1991 | Davis | |
| 5,849,004 A | 12/1998 | Bramlet | |
| 5,882,351 A * | 3/1999 | Fox | A61B 17/1635 606/327 |
| 7,955,392 B2 * | 6/2011 | Dewey | A61B 17/7068 606/248 |
| 8,795,335 B1 * | 8/2014 | Abdou | A61B 17/7065 606/247 |
| 2009/0163920 A1 * | 6/2009 | Hochschuler | A61B 17/7064 606/74 |
| 2011/0178599 A1 * | 7/2011 | Brett | A61F 2/442 623/17.16 |
| 2014/0088711 A1 * | 3/2014 | Chin | A61F 2/30749 623/17.16 |

* cited by examiner

IMPLANT FIXATION SYSTEM AND METHODS

CROSS REFERENCE TO RELATED APPLICATIONS

This application is a continuation under 35 U.S.C. § 120 of International Application No. PCT/EP2014/052568, filed Feb. 10, 2014 (published by the International Bureau as International Publication No. WO/2014/122313 on Aug. 14, 2014), which claims the benefit of U.S. Provisional Application 61/763,392, filed on Feb. 11, 2013. The entire contents of each of the above-referenced patent applications are hereby incorporated by reference.

BACKGROUND

Field of the Invention

The present disclosure relates to medical devices and methods of using and manufacturing the same. More particularly, the disclosure relates to orthopedic devices used to secure implants or other materials to bone. The disclosure also relates to methods for using and manufacturing orthopedic fixation devices.

Description of the Related Art

Knee and hip arthroplasties, as well as other joint replacement surgeries, are becoming increasingly prevalent in our aging society. In joint replacement surgeries, orthopedic implant devices are often used to replace joints that have degenerated, for example, due to traumatic injury or arthritis. Many orthopedic implants, such as the tibial component of a total knee prosthesis, are fixed in the patient by means of an intramedullary stem. Such a stem has certain drawbacks. For example, surgical insertion of an intramedullary stem requires reaming out the medullary cavity of a bone. Such an invasive procedure can cause damage and/or loss of bone stock and bone density in already weakened bones and can result in long recovery times. Moreover, the stems are typically cemented in place, introducing polymer bone cements into the human body. The long-term biocompatibility of these polymer cements has not been fully established. Additionally, fixating an implant in this manner does not correspond with the natural loading, bone growth and bone remodeling mechanisms of the human body. Consequently, the bone stem can loosen over time and may result in implant failure.

To move away from implants having intramedullary stems, an alternative fixation mechanism must be provided. One option is to fixate joint implants to bone using orthopedic bone screws. However, currently available bone screws do not create sufficient force to provide for the long-term fixation of joint implants to bone. Consequently, a need exists for an improved implant fixation device.

SUMMARY

Various implementations of systems, methods, and devices within the scope of the appended claims each have several aspects, no single one of which is solely responsible for the desirable attributes described herein. Without limiting the scope of the appended claims, some prominent features are described herein.

The present application relates generally to orthopedic implant fixation devices and orthopedic implants secured to bone via implant fixation devices. Details of one or more implementations of the subject matter described in this specification are set forth in the accompanying drawings and the description below. Other features, embodiments, and advantages will become apparent from the description, the drawings, and the claims.

One aspect of this disclosure provides an implant fixation device having an engagement element with a concave engagement tip, a guiding element defining a planned trajectory along which the engagement element is configured to move, and an adjustment element coupled to the engagement element or the guiding element and configured to move the engagement element along the planned trajectory.

In some embodiments, moving the engagement element along the planned trajectory moves the engagement element rotationally and translationally. Additionally or alternatively, in some embodiments, moving the engagement element along the planned trajectory causes the concave engagement tip to enter a bone in a first position and rotate within the bone to a second position. In some such embodiments, continuing to move the engagement element along the planned trajectory causes the concave engagement tip to undergo translational movement from the second position to a third position.

In some embodiments of the implant fixation device, the engagement element is a hook. In some embodiments, the adjustment element is a screw. The guiding element of some embodiments is, or includes, a recessed channel or a protruding track, which the engagement element is configured to contact and travel along.

In some embodiments, the implant fixation device includes a plurality of engagement elements and a plurality of guiding elements. In some such embodiments, the adjustment element is coupled to the plurality of engagement elements or the plurality of guiding elements and is configured to move each of the plurality of engagement elements along a planned trajectory defined by the plurality of guiding elements. In this manner, manipulating one adjustment element may cause a plurality of engagement elements to each move along a planned trajectory into a position of engagement with a bone.

Another aspect of the disclosure provides an implant fixation system. In various embodiments, the implant fixation system includes an implant and any one of the implant fixation device embodiments described above.

In some embodiments of the implant fixation system, the concave engagement tip extends from the implant and is configured and positioned for insertion into bone. In some embodiments, the guiding element is or includes a channel or protruding path formed into the implant. Additionally or alternatively, in some embodiments, at least a head portion of the adjustment element extends from the implant and is positioned such that the adjustment element can be accessed and manipulated during surgery when the implant is disposed on or in a bone.

An additional aspect of the disclosure provides a method of fixating an orthopedic implant to bone. The method includes providing an implant fixation system that includes an implant and any one of the implant fixation device embodiments described above. The method further includes positioning the implant on or in a bone and moving the engagement element along the planned trajectory by manipulating the adjustment element.

In some embodiments of the method, moving the engagement element along the planned trajectory causes the concave engagement tip to enter a bone in a first direction, rotate within the bone, and advance further within the bone in a second direction angled from the first direction. In some embodiments, moving the engagement element along the planned trajectory within the bone generates compression forces in the bone and pulls the implant towards the bone.

A further aspect of the disclosure provides a method of manufacturing an implant fixation system. The manufacturing method includes creating a system design. In various embodiments, the system design includes a model of an implant configured to couple with one of the implant fixation device embodiments described above. The method further includes manufacturing at least the implant of the implant fixation system one layer at a time based on the system design.

In some embodiments, the method further includes coupling one of the implant fixation device embodiments described above to the implant. In other embodiments, the system design includes a model of one of the implant fixation device embodiments, and manufacturing at least the implant of the implant fixation system also includes manufacturing the implant fixation device one layer at a time based on the system design.

In some embodiments, the system design is a digital model created on a computer. In some embodiments, manufacturing at least the implant of the implant fixation system is performed using rapid prototyping and additive manufacturing techniques; in some embodiments, it is performed using metal sintering.

In various embodiments, the system design is patient-specific and one or more characteristics of a patient influence the shape, size, and/or configuration of the system design.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Throughout the drawings, similar symbols typically identify similar components, unless context dictates otherwise. Note that the relative dimensions of the following figures may not be drawn to scale.

DETAILED DESCRIPTION OF CERTAIN EMBODIMENTS

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "have," "having," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational and directional terms are used. As recited within this disclosure, the "longitudinal axis" of a bone or component is the elongated axis running through the length of the bone or component.

"Connected" and "coupled," and variations thereof, as used herein include direct connections, such as being contiguously formed with, or glued, or otherwise attached directly to, on, within, etc. another element, as well as indirect connections where one or more elements are disposed between the connected elements. "Connected" and "coupled" may refer to a permanent or non-permanent (i.e., removable) connection.

"Secured" and variations thereof as used herein include methods by which an element is directly secured to another element, such as being glued, screwed, or otherwise fastened directly to, on, within, etc. another element, as well as indirect means of securing two elements together where one or more elements are disposed between the secured elements.

"Proximal" and "distal" are relational terms used herein to describe position from the perspective of a medical professional using an implant fixation device. For example, as compared to "distal," the term "proximal" refers to a position that is located more closely to the medical professional. Often, the proximal end of the fixation device is most accessible to medical professionals during surgery, and includes, for example, the end configured for direct manipulation by surgeons. The distal end opposes the proximal end and often includes, for example, the end configured to be embedded within the bone of a patient.

Embodiments disclosed herein relate to orthopedic implants, as well as fixation devices for securing the implants to bone. The fixation devices of the present invention are configured to engage with both implants and bone and may advantageously be used to secure implants to bone without the need for an intramedullary stem.

The implant fixation devices of various illustrated embodiments are manufactured with, or coupled to, an orthopedic implant to secure the implant to bone. Implant fixation devices described herein include one or more hooks or other concave engagement tip configured to undergo rotational and translational movement within a bone. In various embodiments, each engagement tip is configured to enter cortical bone in a first direction that is relatively transverse to the longitudinal axis of the bone. The engagement tip is configured to rotate as it advances within the bone towards a second direction that is closer to being parallel with the longitudinal axis of the bone. In some embodiments, after rotation, the implant fixation device is configured to direct translational movement of the engagement tip towards the implant, thereby pulling the implant towards the bone. This pull between the implant and the bone generates compression forces on the bone.

Advantageously, the orientation and position of the engagement tips can be altered during surgery, and in some embodiments, even after surgery, allowing the forces exerted on the bone to be at least partially controlled. Various prior art fixation devices, such as conventional bone screws, often extend outward from an implant, entering cortical bone laterally and exerting lateral, tensile forces on the bone. Tensile forces on a bone can lead to poor fixation and further injury. While bone responds poorly to tensile forces, it responds favorably to compression forces. Compression forces have been shown to strengthen bone. When loading on a bone increases, the bone tends to adapt by growing and remodeling itself over time. Such bone growth and remodeling about the site of an implant fixation device may facilitate long-term fixation of the device within the bone. Accordingly, by directing the orientation of the engagement tips in bone, such that the engagement tips pull the implant toward the bone and exert compression forces on the bone, the implant fixation devices disclosed herein are advantageously configured to securely fixate implants. In various embodiments, the implant fixation devices may stimulate bone growth around the site of implantation and facilitate long-term fixation of the implant.

Figure 1A:
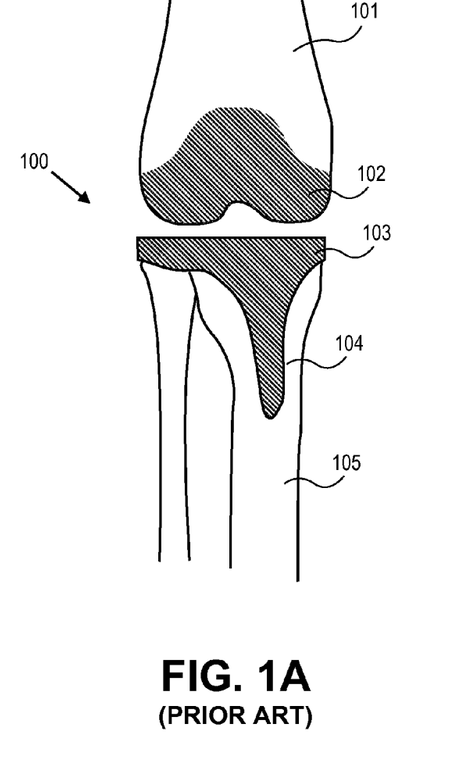
FIG. 1A schematically illustrates the bones of a knee with a total knee prosthesis secured using prior art methods and devices.

FIG. 1A illustrates an example of a knee 100 with a total knee prosthesis secured using prior art methods and devices. The bones surrounding the knee include the femur 101 and the tibia 105. Knee arthroplasty (i.e., total knee replacement surgery) is often performed when cartilage between the femur 101 and the tibia 105, and/or the ends of the bones themselves, erode. In knee arthroplasty, the joint of the knee is replaced, at least by a femoral component implant 102 and a tibial component implant 103. Currently, the tibial component implant 103 typically comprises a long intramedullary stem 104, included to secure the tibial component implant 103 in place. To secure the implant, a patient's medullary canal inside the tibia bone 105 is reamed out and marrow and/or other bone components are removed. Bone cement and the intramedullary stem 104 are then inserted. This is considered an extremely invasive procedure with long and painful recoveries. The embodiments described herein create an improved implant fixation device that eliminate the need for intramedullary stems 104 in at least some joint replacement surgeries.

Figure 1B:
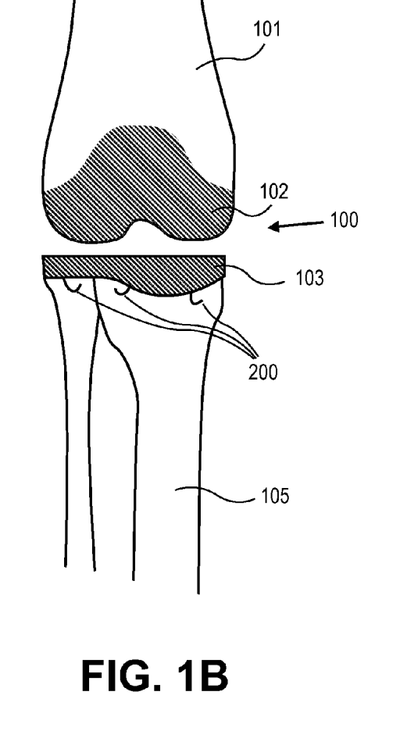
FIG. 1B schematically illustrates the bones of a knee with a total knee prosthesis secured, at least in part, with one embodiment of a presently disclosed implant fixation device.

FIG. 1B illustrates an example of a knee 100 with a tibial component implant 103 secured, at least in part, with one embodiment of an implant fixation device 200. In some embodiments, manipulation by a surgeon causes at least a portion of the implant fixation device 200 to enter the bone 105 in a first direction and move along a planned trajectory which rotates the portion of the implant fixation device 200 that is in the bone to a second direction. Further manipulation by a surgeon may cause translational movement of at least a portion of the implant fixation device 200 in the bone. When oriented in a bone in the second direction, translational movement of the implant fixation device 200 pulls the tibial component implant 103 towards the tibia bone 105, thereby exerting compression forces on the bone 105. This compression force may advantageously stimulate bone growth about the implant fixation device 200 and thus facilitate long-term fixation of the implant 103 without the need for an intramedullary stem.

While the disclosure herein describes an implant fixation device 200 for use with a knee arthroplasty implant, one of skill in the art will readily appreciate that the a fixation device 200 according to various embodiments can equally be used with other joint arthroplasty implants, as well as other partial joint replacement implant devices, and other bone implants more generally. Embodiments including other bone implants are contemplated and hereby expressly incorporated into the present disclosure. The fixation device 200 set forth in this disclosure can be broadly used to secure implants, plates, and/or other materials to bone.

Figure 2A:
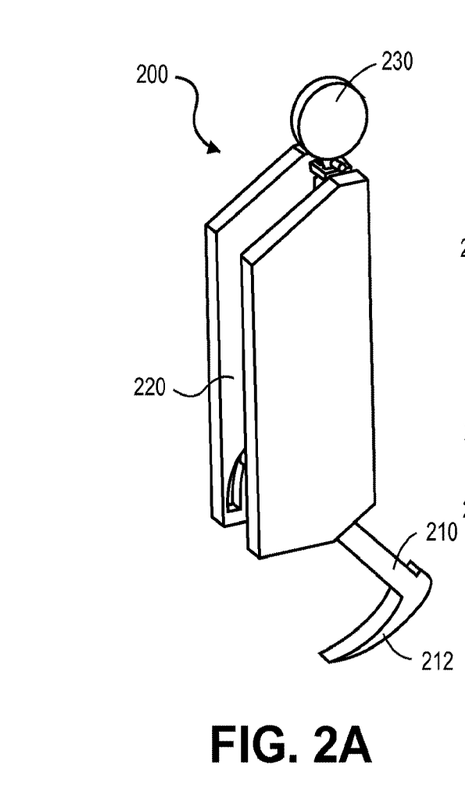
FIG. 2A illustrates a top right perspective view of one embodiment of an implant fixation device positioned within the side walls of an implant.

FIGS. 2A-2D illustrate various views and partial views of one embodiment of an implant fixation device 200. As shown in FIG. 2A, the implant fixation device 200 includes an engagement element 210, which has a hook or other concave engagement tip 212 at the distal-most end. The engagement tip 212 is often tapered to allow the engagement tip 212 to pierce and advance into bone. In some embodiments, the concavity of the engagement tip 212 facilitates rotational displacement of the engagement tip 212 within the bone. In the embodiment illustrated in FIG. 2A, the engagement element 210 is coupled to both a guiding element 220 and an adjustment element 230. The guiding element 220 can be formed of two opposing walls, which in various embodiments, are the walls of an orthopedic implant. The implant providing the walls which form the guiding element 220 can be any size and shape and can be configured for placement on or in any bone. For example, in some embodiments, the guiding element 220 is formed of and within the side walls of a tibia component implant. In other embodiments, the guiding element 220 may be formed of and within the walls of a shoulder implant, a bone plate implant, or any other orthopedic implant known to those skilled in the art. The orthopedic implant of various embodiments is custom built to receive the implant fixation device 200.

Figure 2B:
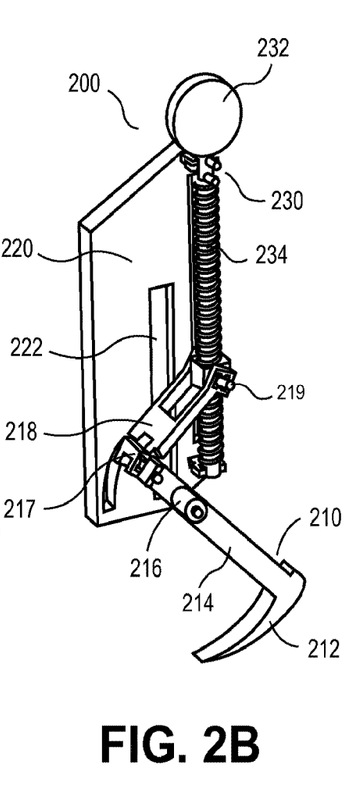
FIG. 2B illustrates a top right perspective view of the implant fixation device embodiment of FIG. 2A with one side wall of the implant removed for improved viewing of the implant fixation device.

In FIG. 2B, one of the implant walls 220 is removed, providing a better view of the engagement element 210, the adjustment element 230, and the remaining portion of the guiding element 220. In the embodiment illustrated in FIG. 2B, the adjustment element 230 is in the form of a screw having a screw head 232 configured for manipulation by a healthcare professional and a threaded screw shaft 234. The engagement element 210 includes the engagement tip 212 and an engagement shaft 214. A connecting element 218 couples the engagement element 210 to the adjustment element 230. In some embodiments, a first end of the connecting element 218 can include one or more through-holes. Similarly, the proximal end of the engagement shaft 214 can include one or more through-holes. In the embodiment illustrated in FIG. 2B, an axle 217 is provided through the set of through-holes, thereby pivotally connecting the engagement element 210 to the connecting element 218. A second end of the connecting element 218 attaches to an annular connector 219. The annular connector 219 of some embodiments is disposed around the screw shaft 234 and includes a pair of projections configured for a pivotal attachment to the second end of the connecting element 218. Accordingly, with such a configuration, the engagement element 210 and the adjustment element 230 are pivotally coupled together. In other embodiments, any suitable mechanism, which achieves pivotal coupling, may be used to directly or indirectly connect the engagement element 210 to the adjustment element 230.

Continuing with FIG. 2B, the engagement element 210 couples to the guiding element 220 via one or more dowels. In the illustrated embodiment, the axle 217 extends beyond the through-holes of the connecting element 218 and acts as an upper dowel. A pin or other protrusion along the engagement shaft 214 acts as a lower dowel 216. The upper dowel (i.e., the axle) 217 and the lower dowel 216 both extend laterally outward from the elongated longitudinal axis of the engagement shaft 214 and are configured for engagement with, and placement within, a channel 222 of the guiding element 220.

Figure 2C:
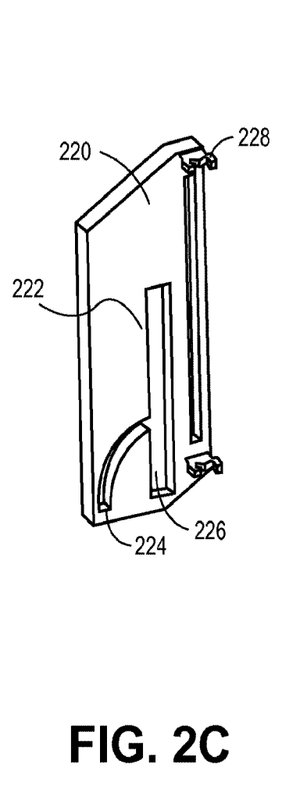
FIG. 2C illustrates a top right perspective view of the implant side wall embodiment of FIG. 2A.

As shown in the implant wall illustration of FIG. 2C, the guiding element 220 defines a channel 222 having a first curved channel portion 224 and a second vertical channel portion 226. In other embodiments, the configuration of the channel 222 may vary in size, orientation, and/or design. In various embodiments, the channel 222 is configured to receive a portion of the engagement element 210 and limit the movement of the engagement element 210 in one or more directions. In the embodiment illustrated in FIG. 2C, both the upper dowel 217 and the lower dowel 216 are positioned within, and confined to, the channel 222. Such confinement restricts movement of the associated engagement element 210. In effect, the channel 222 defines a pre-determined path or trajectory for the engagement element 210. The channel 222 may be formed into the wall of the implant at the time of manufacture. In other embodiments, the channel may be cut or etched into the implant after the initial implant is formed. In still other embodiments, other physical features may be used to define the trajectory of the engagement element 210. For example, in some embodiments, parallel ridges may extend from the guiding element 220, which are configured to receive a portion of the engagement element 210 between the ridges. In other embodiments, a protrusion may extend from the guiding element 220, which has a track or contoured edge along which at least a portion of the engagement element 210 is configured to travel.

Also visible in FIG. 2C is a receiving bracket 228 on the guiding element 220 configured to receive the screw shaft 234 of the adjustment element 230. In the embodiment illustrated in FIG. 2C, the receiving bracket 228 couples to the adjustment element 230 via a snap fit. In other embodiments, other mechanisms for coupling the adjustment element 230 to both the guiding element 220 and the implant may be included.

Figure 2D:
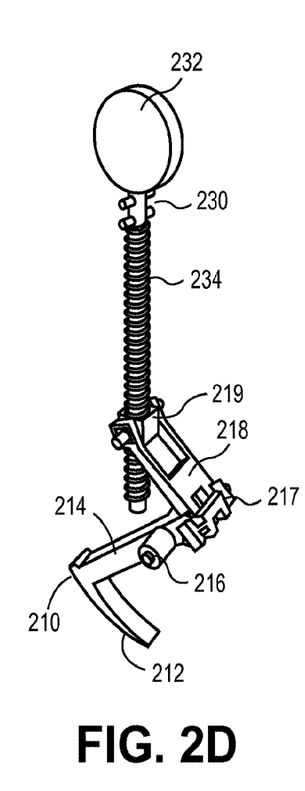
FIG. 2D illustrates a top left perspective view of a portion of the implant fixation device embodiment of FIG. 2A.

The adjustment element (i.e., the screw) 230 and the engagement element 210 are shown most clearly in FIG. 2D. In the provided configuration, the annular connector 219 has internal threading configured to complement the external threading of the screw shaft 234. When a medical professional turns the screw head 234 in one direction, the annular connector 219 is motivated to move up the screw shaft 234. The attached coupling element 218 follows the movement of the annular connector 219, and the coupling element 218 and engagement element 210 pivot in response.

Figure 3A:
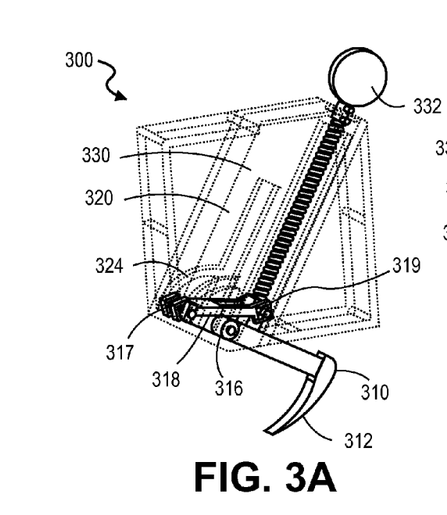
FIG. 3A illustrates a perspective view of one embodiment of an implant fixation device in a first position.

One mechanism by which the elements of the implant fixation device can move relative to one another is provided in more detail in FIGS. 3A-3E. FIG. 3A depicts the initial orientation of one embodiment of an implant fixation device 300 at the time a corresponding implant is placed onto a bone. In the initial orientation, the adjustment element 330 extends through at least a portion of the implant. At least a portion of the engagement element 310, including the engagement tip 312, protrudes from a distal end of the implant. In the illustrated embodiment, a first curved channel portion 324 and a second vertical channel portion 326 are in connection with each other and formed within a wall of the implant. A mirror-image of the first curved channel portion 324 and the second vertical channel portion 326 are formed within an opposing wall of the implant. A first dowel 317 is positioned so as to extend through through-holes within the connecting element 318, through through-holes within the proximal end of the engagement shaft 314, and into the first curved channel portion 324 of both implant walls. The first dowel 317 is positioned at the distal end of the first curved channel portion 324. The second dowel 319 is disposed within the second vertical channel portion 326 of both walls at the distal end. Similarly, the annular connector 319 is disposed around the adjustment element 330 at the distal end of the adjustment element 330. In such a position, the connecting element 318 and the engagement shaft 314 are relatively parallel to each other and relatively perpendicular to the elongated axis of the adjustment element 330. In such a position, the engagement tip 312 is oriented to apply a lateral, tensile force to a bone.

Figure 3B:
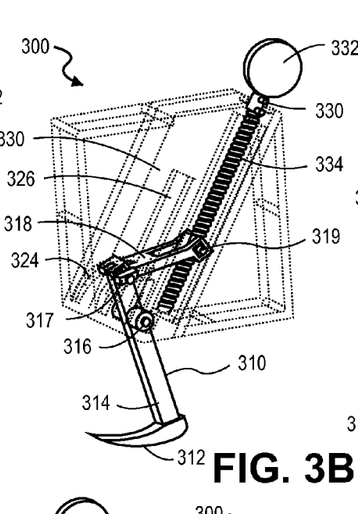
FIG. 3B illustrates a perspective view of the implant fixation device embodiment of FIG. 3A, wherein the implant fixation device is rotating towards a second position.

As shown in FIG. 3B, upon turning the screw head 332, the annular connector 319 moves upward along the threaded screw shaft 334. The connecting element 318, particularly the second end of the connecting element 318, moves upward with the annular connector 319 to which the connecting element 318 is attached. In various embodiments, the connecting element 318 is formed of a substantially rigid material; accordingly, the upward movement of the second end of the connecting element 318 pulls on the engagement shaft 314 of the engagement element 310. Due to the constraints on movement created by the boundaries of the channel 322 in the guiding element 320, the engagement shaft 314 has limited directions in which it can move in response to the forces exerted on it via the connecting element 318. The pull causes the first dowel 317 and proximal end of the engagement shaft 314 to move partially along the first curved channel portion 224. The second dowel 316 remains positioned within the distal end of the second vertical channel portion 226. Accordingly, the second dowel 316 acts as a pivot point around which the engagement element 310 rotates. Such rotation of the engagement element 310 generates torque within the engagement shaft 314 and pushes the engagement tip 312 closer towards, or further into, a bone in a direction angled slightly upwardly from the first position.

Figure 3C:
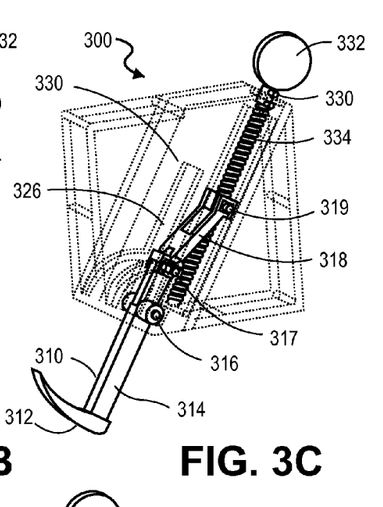
FIG. 3C illustrates a perspective view of the implant fixation device embodiment of FIG. 3A, wherein the implant fixation device is in a second position.

In FIG. 3C, the implant fixation device 300 has reached a second position due to further rotations of the screw head 332. In the second position, the annular connector 319 has progressed further up the threaded screw shaft 334. The upward movement has pulled the connecting element 318 upward and the first dowel 317 has been pulled through the entirety of the first curved channel portion 224 to the second vertical channel portion 226. In such an orientation, the first dowel 317, the second dowel 316, and the elongated longitudinal axis of the engagement shaft 314 are all in alignment with the orientation of the second vertical channel portion 326. In the second position, the engagement tip 312 is angled substantially upward relative to the first position. In some embodiments, the engagement tip 312 can rotate between 15° and 90° in transitioning from the first position to the second position. In other embodiments, the angle of rotation for the engagement tip 312 can be 5°, 100°, or any value therebetween.

Figure 3D:
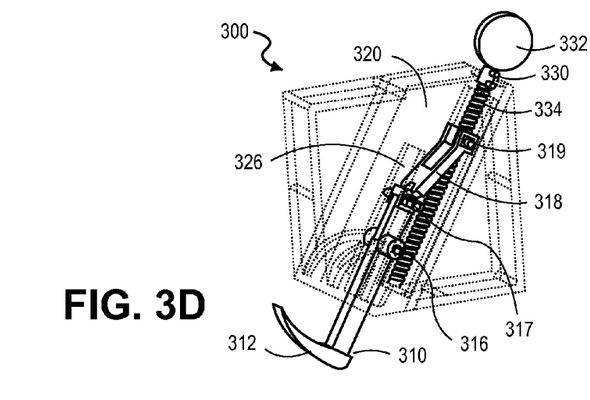
FIG. 3D illustrates a perspective view of the implant fixation device embodiment of FIG. 3A, wherein the implant fixation device is moving towards a third position.

As shown in FIG. 3D, further rotation of the adjustment element/screw 330 leads to translational movement of the engagement member 310. The first dowel 317, the second dowel 316, and the engagement shaft 314 are all moved upward along the same plane as a result of the annular connector 319 moving upward along a parallel plane. It is again the complementary threading between the annular connector 319 and the screw shaft 334, which causes the annular connector to move upward along the screw shaft 334 as the screw 330 is turned. This translational movement causes the engagement tip 312 to retract toward, and at least partially within, the implant. Because the engagement tip 312 is already embedded into bone, preferably, cortical bone, the retraction of the engagement tip 312 towards the implant pulls the implant towards the bone. This pulling of the implant towards the bone exerts compression forces onto the bone.

Figure 3E:
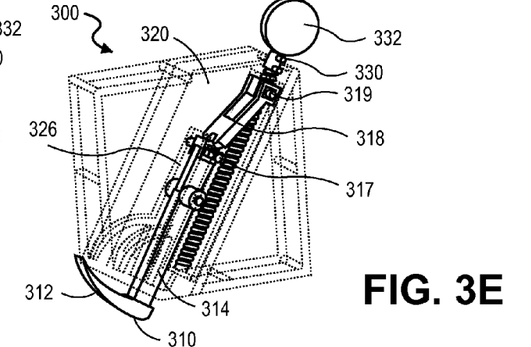
FIG. 3E illustrates a perspective view of the implant fixation device embodiment of FIG. 3A, wherein the implant fixation device is in a third position.

FIG. 3E depicts the implant fixation device 300 in the third position. In the third position, the annular component 319 has reached the proximal end of the screw shaft 334, and the first dowel 317 has reached the proximal end of the vertical channel portion 326. These proximal positions have pulled the engagement shaft 314 upward too. As a consequence, in the third position, the engagement element 310 is nearly fully retracted within the implant. Such a position can serve to limit any tensile forces exerted by the implant fixation device 300. In the illustrated embodiment, nearly all that remains external to the implant is the engagement tip 312, which is well-embedded in the bone. The continued presence of the engagement tip 312 within the bone, pulling the implant towards the bone, allows for implant fixation and the continued generation of compression forces on the bone.

Figure 4A:
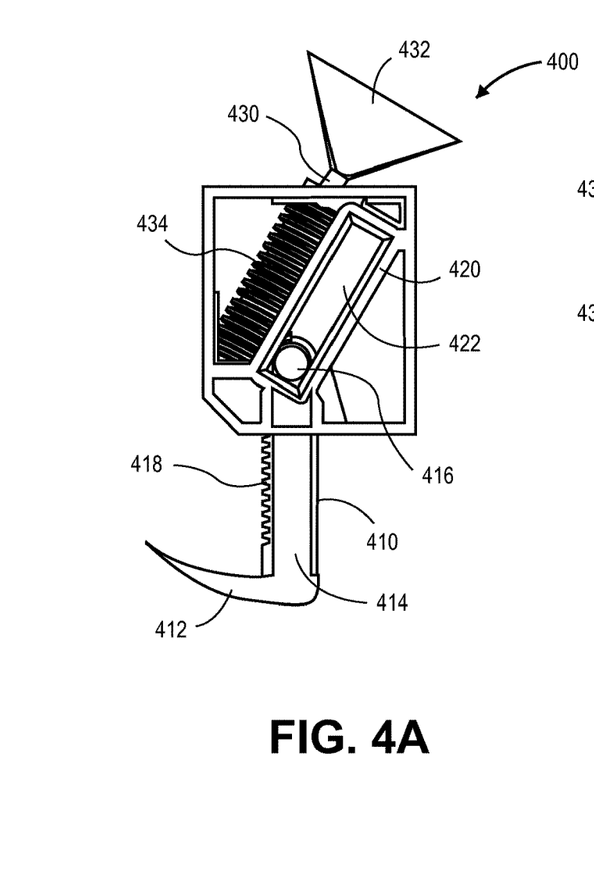
FIG. 4A illustrates a side view of another embodiment of an implant fixation device.

FIG. 4A provides another embodiment of an implant fixation device 400. As with other embodiments described herein, the implant fixation device 400 is configured to be positioned along, or embedded within, an orthopedic implant. The implant fixation device 400 of various embodiments is configured for use with a variety of implants of varying size, shape, and utility. As with other embodiments disclosed herein, the implant fixation device includes an adjustment element 430, a guiding element 420, and an engagement element 410. The engagement element 410 has an engagement tip 412. The implant fixation device 400 is configured to embed the engagement tip 412 within a bone and subject the engagement tip 412 to rotational and translational movement in order to pull the implant towards the bone. By pulling the implant towards the bone, compression forces are generated on the bone.

In the embodiment illustrated in FIG. 4A, the adjustment member 430 is again shaped as a screw, though in other embodiments, any other suitable shape may be used. The adjustment member (i.e., the screw) 430 has a screw head 432 configured for easy handling and manipulation by a medical professional. The screw 430 also includes a threaded screw shaft 434. The screw 430 is positioned against a frame 420, which serves as the guiding member and defines a track or channel 422. The screw 430 and the channel 422 are positioned along parallel planes, which are angled in the desired direction of translation of the engagement element 410 relative to bone.

In the embodiment of FIG. 4A, the engagement element 410 includes an engagement shaft 414 and a dowel 416. The dowel is an extension of the engagement shaft 414, which is positioned at the proximal end of the engagement shaft 414 and protrudes outward so as to engage with the guiding element/frame 420. In the illustrated embodiment, the engagement element 410 is directly coupled to the adjustment element/screw 430 and the guiding element/frame 420 via the dowel 416.

Figure 4B:
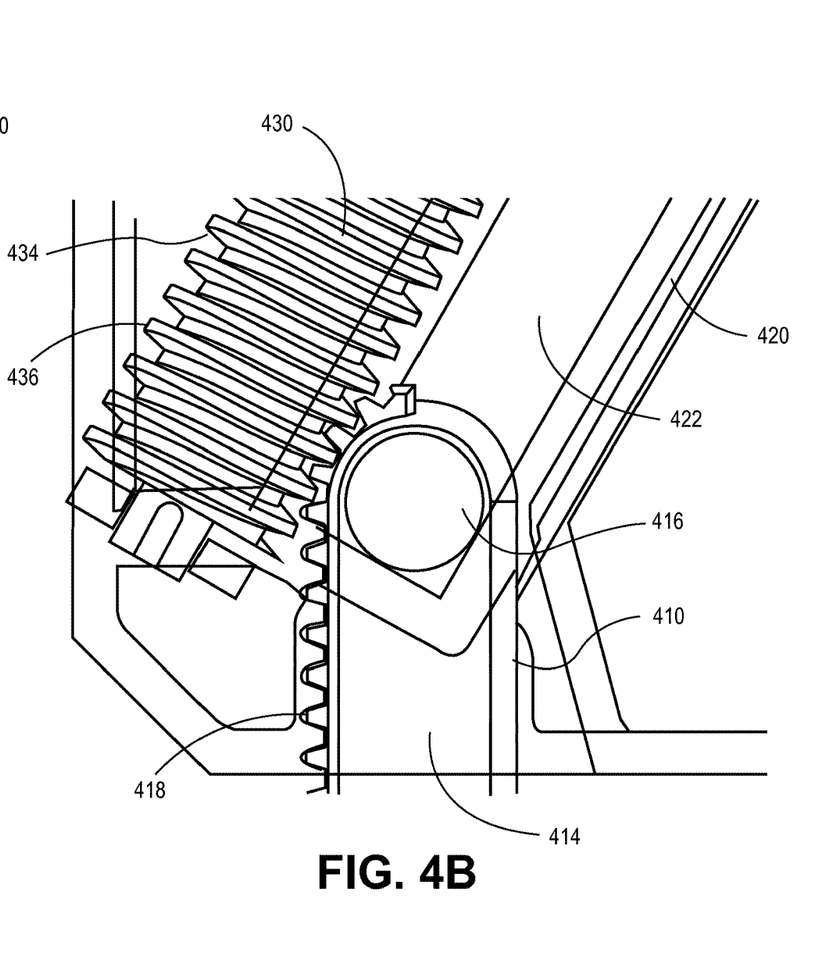
FIG. 4B illustrates a partial view of the implant fixation device embodiment of FIG. 4A, providing a larger view of the coupling mechanisms that exist between the various elements of the implant fixation device.

The area of direct coupling between the engagement element 410, the guiding element 420, and the adjustment element 430, is shown in the partial view of FIG. 4B. As shown, the engagement element 410 directly couples to the guiding element/frame 420 by resting opposing protrusions of the dowel 416 onto opposing struts of the frame 420. The dowel 416 is disposed within the channel 422, and the movement of the dowel 416 is limited to translational movement along the channel 422. The engagement shaft 414 of the current embodiment has a surface at least partially lined with a plurality of teeth 418. These teeth 418 are configured for coupling with and between the threads 436 disposed around the shaft 434 of the screw 430. As the screw 430 is turned, the complementary interaction between the teeth 418 and the threading 436 causes the teeth 418, and accordingly, the engagement element 410, to advance upward along the threading 436. In the illustrated embodiment, engagement between the teeth 418 of the engagement element 410 and the threads 436 of the screw shaft 434, first cause the engagement element 410 to rotate about the dowel 416 until the engagement shaft 414 and the screw shaft 434 are in parallel alignment. This rotation kicks the engagement tip 412 towards the direction of the bone and leads to rotation of the engagement tip 412. Once the engagement shaft 414 and the screw shaft 434 are in parallel alignment, all subsequent motion is translational movement advancing the engagement element 410 upwards. This translational movement retracts the engagement element 410 at least partially into the implant and pulls the implant towards the bone.

While turning or manipulating the adjustment element is described as leading to rotational movement of the engagement element toward the bone and/or upward translational movement, one of skill in the art will understand that the adjustment element embodiments disclosed herein may additionally or alternatively be configured to cause downward translational movement and rotational movement away from the bone when the adjustment element is rotated in the opposite direction. The ability to move the engagement element downward and away from the bone may be helpful when loosening and/or adjusting the fixation of the implant to the bone.

Figure 5A:
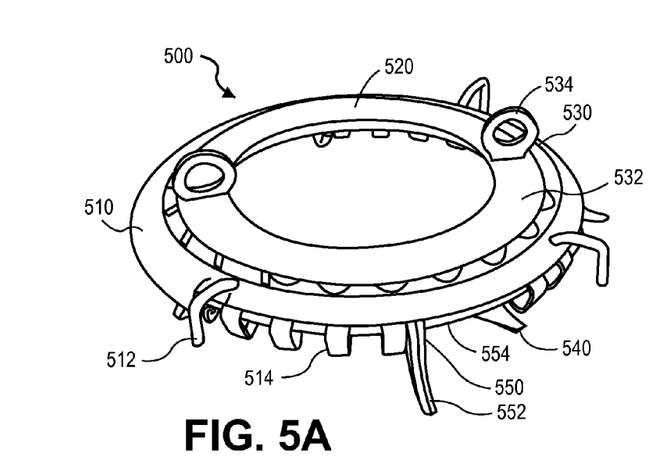
FIG. 5A illustrates a top perspective view of one embodiment of an implant fixation system, which includes one embodiment of a tibial component implant and one embodiment of an implant fixation device.
Figure 5B:
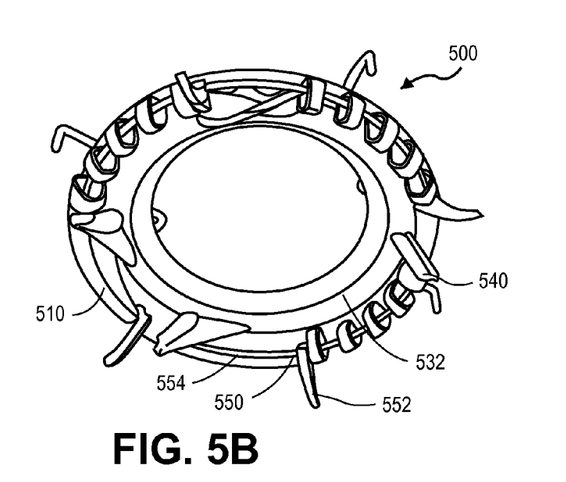
FIG. 5B illustrates a bottom perspective view of the implant fixation system of FIG. 5A.

FIGS. 5A and 5B depict top and bottom perspective views, accordingly, of one embodiment of an implant fixation system 500. The implant fixation system 500 includes an implant fixation device 520 and an implant 510. In the depicted embodiment, the implant 510 is a tibial component implant; however, in other embodiments, a plurality of different implants are used. The depicted implant 510 can be positioned onto the top surface of the tibia with the aid of stabilizing elements 512. The stabilizing elements 512 can be configured to at least partially wrap around an edge of the tibia's top surface. In various embodiments, the implant 510 can be configured to remain in a fixed position relative to the bone.

The implant fixation device 520 includes an engagement element 550, a guiding element 540, and an adjustment element 530. The adjustment element 530 includes a rotatable disk 532 and one or more extension loops 534 extending proximally from the rotatable disk 532. The extension loops 534 can be configured to facilitate grasping and rotating of the disk 532. The guiding element 540 can be fixed to, and configured to rotate with, the rotatable disk 532. The rotatable disk 532 can be configured to rotate relative to the implant 510 and the engagement element 550. In the illustrated embodiment, the engagement element 550 includes a concave engagement tip 552 and a tubular ring 554. The engagement tip 552 can be configured to pivot about the ring 554. In some embodiments, the tubular ring 554 is disposed at least partially within the implant 510 and held in place by the implant 510. For example, in the depicted embodiment, a plurality of securement elements 514 extending from the implant 510 are disposed around the ring 554, holding the tubular ring 554 in place.

Figure 5C:
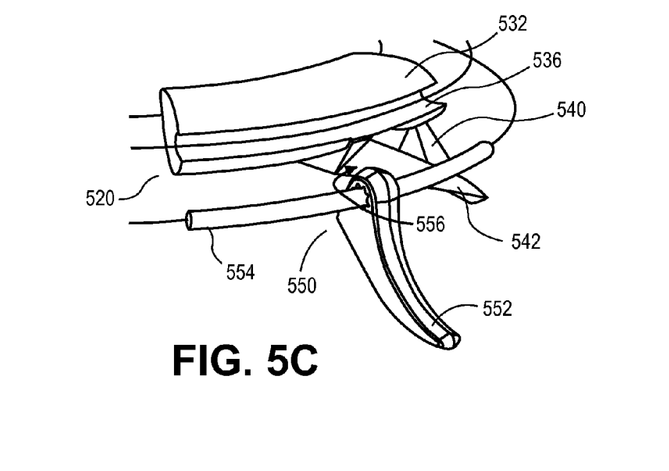
FIG. 5C illustrates a top left perspective partial view of the implant fixation device embodiment of FIG. 5A.
Figure 5D:
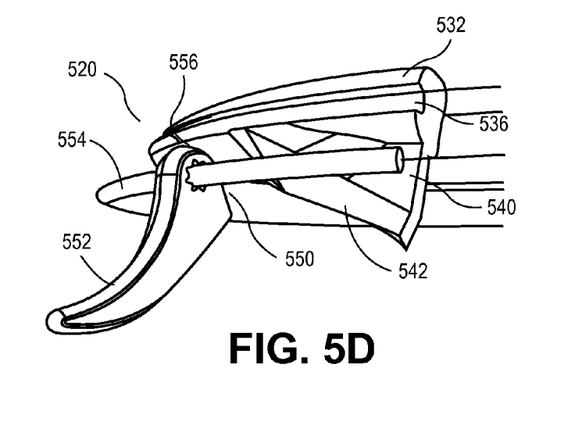
FIG. 5D illustrates a top right perspective partial view of the implant fixation device embodiment of FIG. 5A.

FIGS. 5C and 5D illustrate cutaway views providing a closer look at the interplay between the engagement element 550, the guiding element 540, and the adjustment element 530 of the implant fixation device 520 included in the illustrated embodiment. As described above, the adjustment element 530 includes a rotatable disk 532. The rotatable disk 532 is configured to receive a portion of the implant 510 within an outer groove 536 and rotate or slide relative to the implant. The rotatable disk 532 also rotates relative to the engagement element 550. The guiding element 540 of the illustrated embodiment is a protruding tab, which is fixed directly to the rotatable disk 532. The guiding element/tab 540 includes a contoured surface 542. Upon rotation of the rotatable disk 532, the contoured surface 542 comes into contact with, and pushes on, an inner edge 556 of the concave engagement tip 552. The pushing of the contoured surface 542 against the inner edge 556 of the engagement tip 552 induces the engagement tip 552 to pivot. In some embodiments, the contoured surface 542 of the guiding element 540 is sized and shaped so as to induce a planned degree of pivot by the engagement tip 552. The contoured surface 542 may have multiple slopes along each guiding element/tab 540 so as to cause the engagement tip 552 to pivot by varying degrees as the guiding element/tab 540 slides by the engagement tip 552. In this manner, the contoured surface 542 defines a planned path along which the engagement tip 552 is configured to travel.

Figure 6:
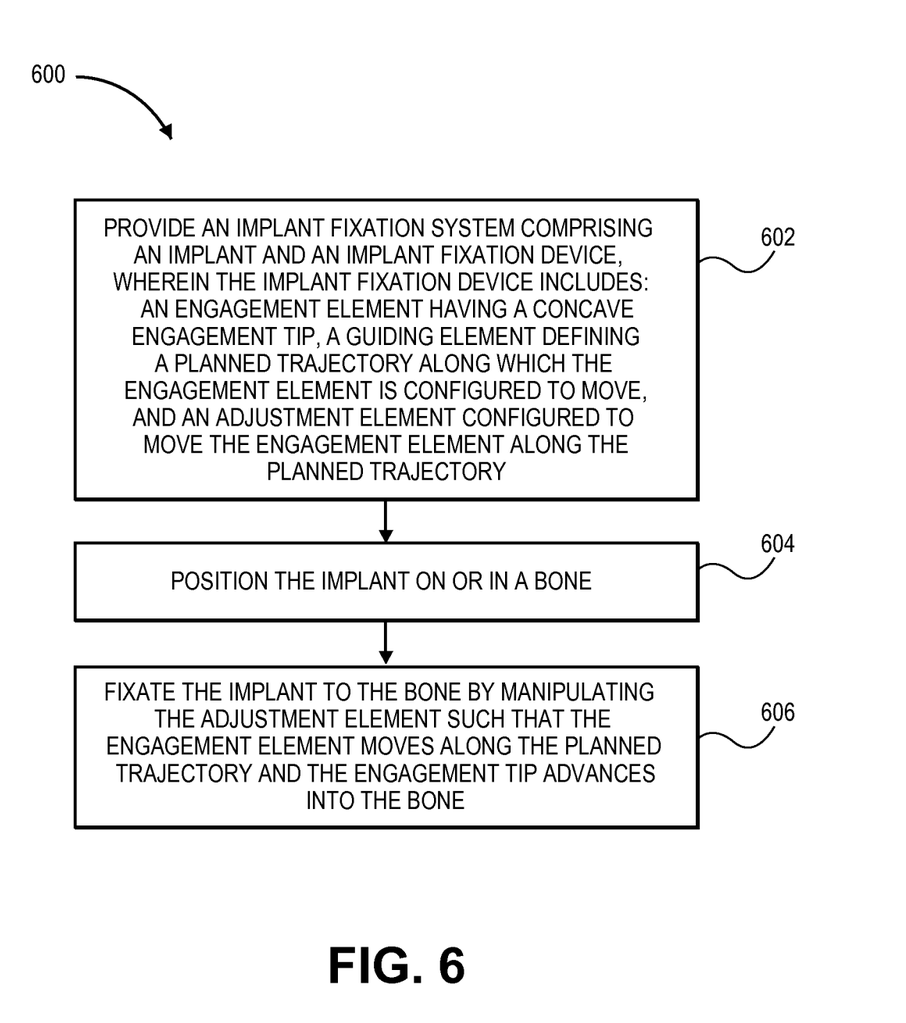
FIG. 6 illustrates a flow diagram depicting one embodiment of a method for fixating an orthopedic implant to bone.

FIG. 6 illustrates a flow diagram 600 outlining one method of fixating an orthopedic implant to bone. In describing the method, reference will be made to the implant fixation system 500 of FIG. 5A, for illustrative purposes only. Any suitable implant fixation system may be used.

As shown at block 602, in one embodiment, the method includes providing or obtaining an implant fixation system 500. The implant fixation system 500 includes an implant 510 and an implant fixation device 520. The implant fixation device 520 includes: an engagement element 550 having a concave engagement tip 552, a guiding element 540 defining a planned trajectory along which the engagement element 550 is configured to move, and an adjustment element 530 configured to move the engagement element 550 along the planned trajectory. Any implant fixation device embodiment described in this disclosure is suitable for this method of implant fixation.

At block 604, the implant 510 can be positioned on or in a bone, such as, for example, on the exposed top surface of the tibia. At block 606, the implant 510 can be fixated to the bone using the implant fixation device 520. Particularly, in various embodiments of the method, the adjustment element 530 is manipulated by a surgeon or other medical professional. In some embodiments, the adjustment element includes a screw, which is manipulated by a medical professional by turning the head of the screw. In other embodiments, the adjustment element 530 includes a rotatable disk 532, which can be rotated, for example, with the aid of an extension loop 534 protruding proximally from the rotatable disk 532. In still other embodiments, other adjustment elements employing different adjustment mechanisms can be used and manipulated by the medical professional.

In various embodiments, manipulating the adjustment element causes the engagement element to move along a planned trajectory defined by the guiding element. In some embodiments, each adjustment element is coupled to one engagement element or one guiding element. When each adjustment element is independently coupled to one engagement element or one guiding element, the medical professional can independently adjust each implant fixation device. Such a configuration provides the medical professional with the greatest amount of flexibility and control over fixation, allowing the medical professional to choose the order and speed with which each implant fixation device is fixated to the bone. The independent configuration also allows the medical professional to loosen one implant fixation device at a time, as needed, to adjust the implant without loosening every implant fixation device.

In other embodiments, such as, for example, the embodiment illustrated in FIG. 5A, each adjustment element 530 can be coupled to a plurality of engagement elements 550 or a plurality of guiding elements 540. In some such embodiments, there are equal numbers of engagement elements 550 and guiding elements 540, and each engagement element 550 corresponds to a distinct guiding element 540. In such embodiments, when the adjustment element 530 is manipulated, it moves each of the plurality of engagement elements 550 into contact with a track or contoured surface 542 in the corresponding guiding element 540 (if not already in contact with the track or contoured surface 542). Manipulation of the adjustment element 530 then moves each engagement element 550 along the path defined by the track or contoured surface 542. When one adjustment element 530 is configured to move a plurality of engagement elements 550 or guiding elements 540, the time it takes to fixate the implant is reduced. In some embodiments, the implant fixation device 520 is configured to move all engagement elements 550 along their respective paths simultaneously. In other embodiments, the implant fixation device 520 is configured to move the engagement elements 550 along their respective paths sequentially or in any other suitable pattern or order. The implant fixation device 520 may be configured to move some or all of the engagement elements 550 at an equal speed or at different speeds.

When the implant 510 is positioned in or on a bone, moving the engagement element 550 along the planned trajectory defined by the guiding element 540 can cause the concave engagement tip 552 to enter the bone in a first position and rotate within the bone to a second position. In some embodiments, continuing to move an engagement element along the planned trajectory causes the concave engagement tip to undergo translational movement from the second position to a third position, thereby pulling the implant towards the bone and exerting compression forces on the bone.

For implants in the legs, additional compression forces are present during walking, running, and other physical activity, when the weight of a patient bears down onto the implant, applying further loading on the bone. When loading on a bone increases over time, the bone tends to adapt by growing and remodeling itself. Such bone growth and remodeling about the site of the implant fixation device may facilitate long-term fixation of the device within the bone.

In some embodiments, additional methods and features may be employed in order to increase load overtime and aid long-term fixation. Particularly, additional methods and features may be employed to increase load during the initial stages of recovery after surgery when the patient has limited mobility and limited options for increasing load naturally. For example, in some embodiments, the method of fixating the implant to bone may additionally include further adjusting the position and/or orientation of the implant fixation device non-invasively post-surgery. In some embodiments, the position and/or orientation may be adjusted non-invasively through the application of one or more magnets near the surgical site. In other embodiments, a physical connection may exist between the upper and lower implants, for example, between the femoral and tibial implant components, which is configured to adjust the load exerted by each component onto the respective bones over time. In still other embodiments, the implant may include a button, which, when pressed or activated, causes the engagement element to translate from a third position towards a fourth position. Each pressing or activation of the button may move the engagement element closer to the fourth position until the fourth position is finally reached. The button may be pressed or activated externally via a magnet, near-field communications, Bluetooth, or other wireless communication or it may be activated internally via mechanical activation. For example, as used in the first few days of recovery from knee surgery, the button may be activated each time a patient straightens his or her knee. These additional load-inducing examples are provided for illustrative purposes only; additional methods and features for increasing load within the implant site will be apparent to those having skill in the art, and such methods and features are contemplated and incorporated herein.

Figure 7:
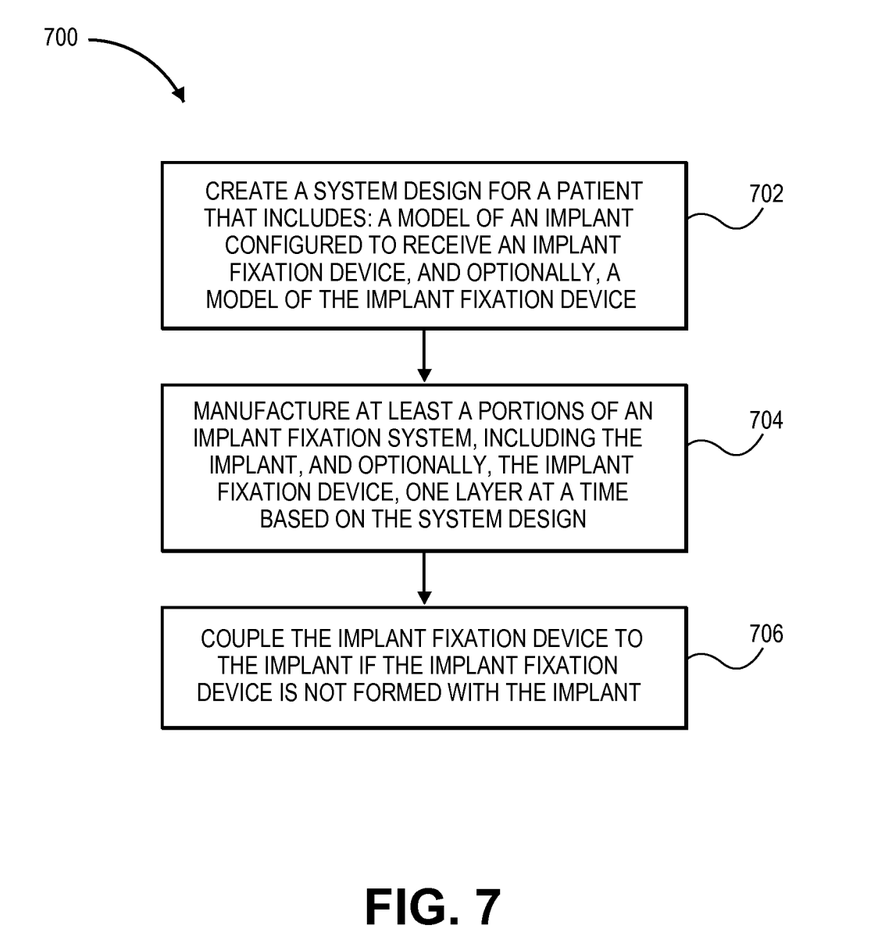
FIG. 7 illustrates a flow diagram depicting one embodiment of a method of manufacturing an implant fixation system.

FIG. 7 illustrates a method of manufacturing an implant fixation system. At block 702, the method includes creating a system design that includes a model of an implant configured to receive an implant fixation device, and optionally, a model of the implant fixation device. In some embodiments, the system design is a digital model formed on a computer. At block 704, the method includes manufacturing at least part of the implant fixation system, including the implant, and optionally, the implant fixation device, one layer at a time based on the system design. At block 706, the implant fixation device is coupled to the implant if the implant fixation device was not formed with the implant.

It is to be understood here, as it is understood throughout this disclosure, that the implant and any computer model of the implant may be configured to receive a plurality of implant fixation devices. None, some, or all of said implant fixation devices may be formed one layer at a time with the implant based on the system model. For example, in some embodiments, the implant is designed and formed to receive a plurality of implant fixation devices, but at least portions of the implant fixation devices are manufactured separately and coupled to the implant during or after manufacture of the implant. In particular, in some embodiments, the channels of the guiding elements are formed into the walls of the implant, but the adjustment elements and engagement elements are formed separately. Receiving holes, bores, brackets, or other receiving features may be formed into the implant to couple the adjustment elements and/or engagement elements to the implant. Additionally or alternatively, the implant and components of the implant fixation devices may be coupled together via any suitable fixation means such as, for example, welding or overmolding.

In other embodiments, the implant and one or more implant fixation devices are first designed as a digital model, then formed together, one layer at a time, in accordance with the design of the digital model. In such embodiments, the implant fixation system may be contiguously fabricated (e.g., formed from a single additive manufacturing process).

The design of the orthopedic implant or the entire implant fixation system may be personalized by taking into account patient-specific features during the design and modeling process. For example, one or more of: the size and shape of the implant, the number and positioning of the implant fixation devices, and the size and shape of the implant fixation devices may be tailored according to the size, density, and disease state of the bone, the size, age, and activity level of the patient, and/or the location of the implant. Similarly, the material(s) used to form the implant and the implant fixation devices may be tailored in accordance with such factors.

In some embodiments, the implant and/or the implant fixation system is partially or completely made by additive manufacturing. Additive manufacturing creates a three-dimensional (3-D) object by laying down successive layers of material. Advantageously, this manufacturing method allows for the creation of an integrated system. Additive manufacturing technologies enable the manufacturing of intricately detailed devices at a sufficiently small scale to be useful for orthopedic fixation. Additionally, with additive manufacturing, the 3-D object is often created directly from a digital model. Building from a digital model rather than, for example, a pre-formed mold, allows for relatively quick and inexpensive personalization and modification of the design. Accordingly, additive manufacturing allows for the integration of patient-specific features. For converting the design's digital image information into a three-dimensional object, any suitable technique known in the art may be used, such as, for example, a rapid prototyping technique.

Rapid Prototyping and Manufacturing (RP&M) may be defined as a group of techniques used to quickly fabricate a scale model of an object typically using three-dimensional (3-D) computer aided design (CAD) data of the object. Currently, a multitude of Rapid Prototyping techniques are available, including, for example, stereolithography (SLA), Selective Laser Sintering (SLS), Fused Deposition Modeling (FDM), and foil-based techniques.

A common feature of these techniques is that objects are typically built layer by layer. Stereolithography, presently the most common RP&M technique, utilizes a vat of liquid photopolymer "resin" to build an object one layer at a time. On each layer, an electromagnetic ray (e.g. one or several laser beams that are computer-controlled), traces a specific pattern on the surface of the liquid resin, the pattern defined by the two-dimensional cross-sections of the object to be formed. Exposure to the electromagnetic ray cures, or solidifies, the pattern traced on the resin and adheres it to the layer below. After a coat had been polymerized, the platform descends by a single layer thickness and a subsequent layer pattern is traced, adhering to the previous layer. A complete 3-D object can be formed by this process.

Fused deposition modeling (FDM) and related techniques make use of a temporary transition from a solid material to a liquid state, usually due to heating. The material is driven through an extrusion nozzle in a controlled way and deposited in the required place as described, for example, in U.S. Pat. No. 5,141,680, the entire disclosure of which is hereby incorporated by reference.

Foil-based techniques fix coats to one another by means of gluing or photo polymerization or other techniques and cut the object from these coats or polymerize the object.

Typically, RP&M techniques start from a digital representation of the 3-D object to be formed. Generally, the digital image is sliced into a series of cross-sectional layers which can be overlaid to form the object as a whole. The RP&M apparatus uses this data for building the object on a layer-by-layer basis. The cross-sectional data representing the layer data of the 3-D object may be generated using a computer system and computer aided design and manufacturing (CAD/CAM) software.

A selective laser sintering (SLS) apparatus may be used for the manufacture of an orthopedic anchoring device template, instead of a computer model. Selective laser sintering (SLS) uses a high power laser or another focused heat source to sinter or weld small particles of plastic, metal, or ceramic powders into a mass representing the 3-D object to be formed. It should be understood however, that various types of rapid manufacturing and tooling may be used for accurately fabricating these orthopedic anchoring devices including, but not limited to, stereolithography (SLA), Fused Deposition Modeling (FDM) or milling.

The implant fixation systems described above (or parts thereof) may be manufactured using different materials. In some embodiments, if SLS is used as a RP&M technique, the orthopedic anchoring device may be fabricated from a polyamide such as PA 2200 supplied by EOS, Munich, Germany. In other embodiments, any material known by those skilled in the art, which is suitable for use with orthopedic implants and suitable for use in additive manufacturing, may be used. In some embodiments, only materials that are biocompatible (e.g. USP class VI compatible) with human bone are used. In some embodiments, the implant fixation device may be formed from any biocompatible material that attaches well to bone. In some embodiments, polylactic acid (PLA), polyether-ether-ketone (PEEK), titanium, or any other suitable plastic, metal, metal alloy, or composite material may be used to form all or part of the implant fixation system. In some embodiments, at least portions of the implant and/or implant fixation devices are formed of bioabsorbable materials. In such embodiments, non-force-generating portions of the implant and/or implant fixation devices may be porous to encourage bone growth in and around such portions of the implant fixation system.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

While this invention has been described in connection with what are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While the present disclosure has described certain exemplary embodiments, it is to be understood that the invention is not limited to the disclosed embodiments, but, on the contrary, is intended to cover various modifications and equivalent arrangements included within the scope of the appended claims, and equivalents thereof.

What is claimed is:

1. An implant fixation device for fixating an implant, comprising:
    an engagement element comprising a plurality of teeth and a concave engagement tip for entering cortical bone;
    a guiding element defining a planned trajectory along which the engagement element is configured to move such that the concave engagement tip is configured to enter into the cortical bone in a first direction and rotate within the cortical bone by moving between a first position and a second position thereby causing tensile forces within the cortical bone, and such that the concave engagement tip is configured to undergo translational movement in a second direction while disposed in the cortical bone from the second position to a third position thereby relieving the tensile forces within the cortical bone and causing compressive forces on the cortical bone by retracting the concave engagement tip and the attached cortical bone toward the implant; and
    an adjustment element comprising a plurality of threads and coupled to the engagement element or the guiding element and configured to move the engagement element along the planned trajectory, wherein complementary interaction between the plurality of teeth and the plurality of threads causes the engagement element to advance along the threads and to move along the planned trajectory, thereby causing the engagement element to both rotate between the first position and the second position and translate between the second position and the third position.

2. The implant fixation device of claim 1, wherein the engagement element is a hook.

3. The implant fixation device of claim 1, wherein the adjustment element is a screw.

4. The implant fixation device of claim 1, wherein the guiding element comprises a recessed channel or a protruding track which the engagement element is configured to contact and travel along.

5. An implant fixation system for fixating an implant to a bone comprising cortical bone, comprising:
an implant;
an engagement element comprising a plurality of teeth and a concave engagement tip for entering the cortical bone;
a guiding element defining a planned trajectory along which the engagement element is configured to move such that the concave engagement tip is configured to enter into the cortical bone in a first direction and rotate within the cortical bone by moving between a first position and a second position thereby causing tensile forces within the cortical bone, and such that the concave engagement tip is configured to undergo translational movement in a second direction while disposed in the cortical bone from the second position to a third position thereby relieving the tensile forces within the cortical bone and causing compressive forces on the cortical bone by retracting the concave engagement tip and the attached cortical bone toward the implant; and
an adjustment element comprising a plurality of threads and coupled to the engagement element or the guiding element and configured to move the engagement element along the planned trajectory, wherein complementary interaction between the plurality of teeth and the plurality of threads causes the engagement element to advance along the threads and to move along the planned trajectory, thereby causing the engagement element to both rotate between the first position and the second position and translate between the second position and the third position.

6. The implant fixation system of claim 5, wherein the concave engagement tip extends from the implant and is configured and positioned for insertion into the bone.

7. The implant fixation system of claim 5, wherein the guiding element comprises a channel or protruding path.

8. The implant fixation system of claim 5, wherein at least a head portion of the adjustment element extends from the implant and is positioned such that the adjustment element can be accessed and manipulated during surgery when the implant is disposed on or in the bone.

\* \* \* \* \*